United States Patent [19]

Fele et al.

[11] Patent Number: 4,766,079

[45] Date of Patent: Aug. 23, 1988

[54] METHOD OF USING POLYPROPYLENE GLYCOL TO IMPROVE MOVEMENT AND INTERMIXTURE OF BLOOD AND OTHER FLUIDS IN CAPILLARY TUBES

[75] Inventors: Karl Fele, Varberg; Stellan Lindberg, Förslöv, both of Sweden

[73] Assignee: Biolabimex AB, Varberg, Sweden

[21] Appl. No.: 863,376

[22] PCT Filed: Sep. 9, 1985

[86] PCT No.: PCT/SE85/00334

§ 371 Date: May 1, 1986

§ 102(e) Date: May 1, 1986

[87] PCT Pub. No.: WO86/01891

PCT Pub. Date: Mar. 27, 1986

[30] Foreign Application Priority Data

Sep. 11, 1984 [SE] Sweden ............................ 8404538

[51] Int. Cl.$^4$ ........................................... G01N 33/48
[52] U.S. Cl. ...................................... 436/63; 424/101; 435/2; 436/68; 436/70; 137/13
[58] Field of Search ......................... 424/101; 137/13; 436/63, 70; 435/2

[56] References Cited

U.S. PATENT DOCUMENTS 3,736,288  5/1973  Stratta et al. ..................... 137/13

OTHER PUBLICATIONS

Giles et al–Chem. Abst., vol. 76 (1972), p. 142005y.
Vander Meulen–Chem. Abst., vol. 83 (1975), p. 12862j.
McClaflin et al–Chem. Abst., vol. 83 (1975), p. 118,399d.

Primary Examiner—Sam Rosen
Attorney, Agent, or Firm—Harness, Dickey & Pierce

[57] ABSTRACT

A method of neutralizing the electrostatic forces in liquids or solutions in liquid phase, preferably blood and blood solutions, respectively. The electrostatic forces primarily consist of surface tension and interrepellant forces between particles in the solution.

The purpose of the invention is obtained by adding polypropylene glycol $H[OCH(CH_3)CH_2]_nOH$ to the liquid or solution. Polypropylene glycol possesses properties allowing it to neutralize the electrostatic forces without affecting the red blood cells.

6 Claims, 3 Drawing Sheets

METHOD OF USING POLYPROPYLENE GLYCOL TO IMPROVE MOVEMENT AND INTERMIXTURE OF BLOOD AND OTHER FLUIDS IN CAPILLARY TUBES

BACKGROUND OF THE INVENTION

The subject invention relates to a method which improves the movement of blood and other fluids and their intermixture in tubes where the surface tension is strong, and this without damage being done to the blood corpuscles. The invention also allows the use of thinner-bore tubes or less energy-consuming pumps in continuous-flow systems without change of the character of the fluids passing through systems of this kind.

In the health service, particularly in laboratories, capillary tubes are often used for collection of blood. To prevent the blood from coagulating it is customary to add double-acting solutions, i.e. anti-coagulants and thinning agents.

The strong surface tension that exists in capillary tubes causes problems in achieving inter-mixture of blood and solutions added thereto. For this reason techniques such as magnetic stirring, manual and mechanic vibrating and shaking methods are used to obtain satisfactory degrees of intermixture. However, these methods often lead to bursting of the blood corpuscles, resulting in undesirable haemolysis, which has a detrimental effect on the subsequent analysis of the blood.

Surface tension in capillary tubes may be reduced by means of various kinds of surfactants. However, surfactants too, have an haemolytical effect on blood corpuscles and interfer with other analysis reactants and therefore are used very sparingly.

Capillary tubes are also used within the health service to carry and transport blood and other fluids in so called continuous flows. In order to separate blood samples from one patient from blood samples from other patients or from other fluids which are flowing simultaneously in the same tube these fluids are separated with the aid of gas bubbles (FIG. 1).

Gas bubbles and solutions channelled through tubes of this kind are affected by the strong surface tension therein. The larger the amount of bubbles in the tubes and the longer the tube the larger the total surface tension that must be overcome. For this purpose large and energy-consuming pumps are used, e.g. peristaltically operating pumps, or else larger-bore tubes are chosen for the purpose of reducing the effects of the surface tension.

SUMMARY OF THE INVENTION

The purpose of the subject invention is:
to completely or partially block the effects of the surface tension in capillary tubes to allow easy intermixture of blood and other fluids without detrimental effects on the blood corpuscles;
to reduce the need of mechanical aids to effect the mixing;
to reduce the effects of surface tension of gas bubbles and other fluids in continuous-flow systems so that
(a) the risks of undesired haemolysis are reduced;
(b) thinner capillary tubes may be used;
(c) less energy-consuming pumps may be used.

This is achieved in accordance with the teachings of the invention by adding polypropylene glycol H[OCH(CH$_3$)CH$_2$]$_n$OH to reduce the electrostatic forces, e.g. surface tension, in liquids or solutions in liquid phase, such as blood and blood solutions.

Polypropylene glycol may be added when blood is mixed with a solution designed to facilitate dispersion of the blood in said soluton.

Polypropylenelglycol may also be added to said liquid or said solution to reduce the surface tension thereof when the liquid or the solution is conducted through capillary tubes.

In the performance of analyses involving sedimentation of a liquid, polypropylene glycol may be added to reduce the repellant forces existing between the particles forming the sediment. A particular application is to us polypropylene glycol to facilitate the rouleaux formation of clustered red cells.

BRIEF DESCRIPTION OF THE DRAWINGS

In order to illustrate the invention the method described above will be explained in closer detail with reference to the accompanying drawings.

In the drawings.

DETAILED DESCRIPTION OF A PREFERRED EMBODIMENT

Figure 2:
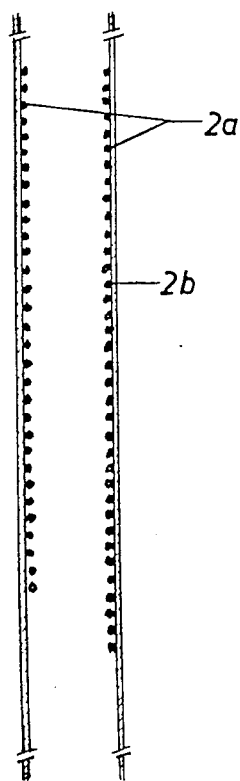
FIG. 2 shows a capillary tube (2b) which is treated on its inside face with polypropylene glycol (2a) in accordance with the teachings of the invention.
Figure 3:
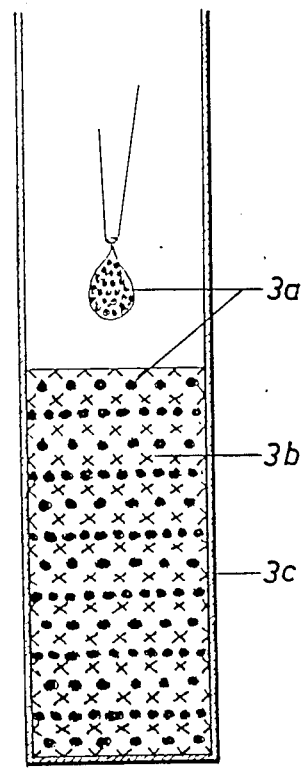
FIG. 3 illustrates a capillary tube (3c) to which has been added polypropylene glycol (3a) to be mixed with another fluid (3b) inside the tube. The result is that the surface tension is partially or completely abolished and for this reason intermixture with any further fluid (3d) which is added to the first solution (3b) is facilitated.
Figure 1:
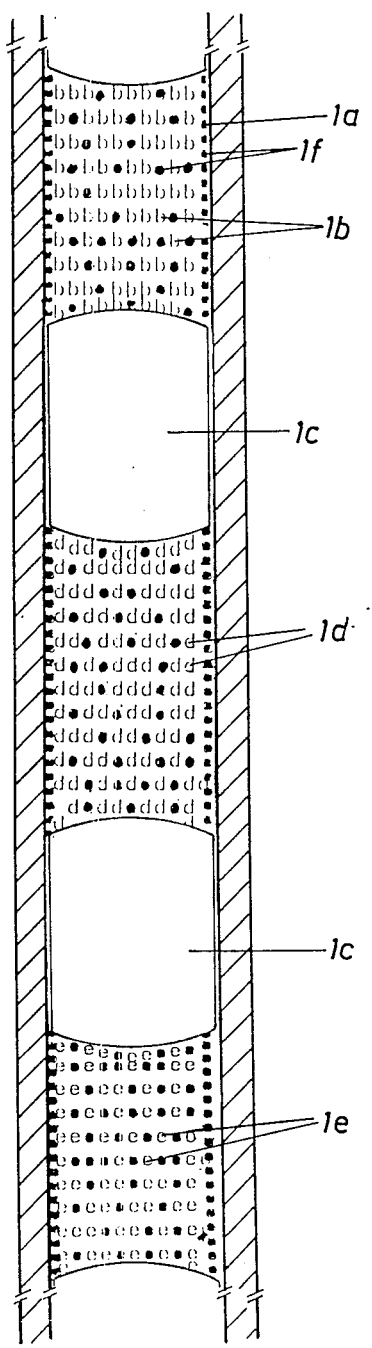
FIG. 1 shows a continuous-flow system wherein one or several fluids (1b, 1d, 1e) are separated from each other by means of gas bubbles (1c) in a capillary tube. When a tube of this kind is treated with polypropylene glycol (1f) the latter will deposit on the inner face of the capillary tube (1a), thus reducing the surface tension without reaction with the fluid contained in the tube.

By adding polypropylene glycol (PPG) which is a solution of inert character, to capillary tubes (FIG. 2) or to the fluid contained in such tubes (FIG. 3) the solution will be prevented from penetrating into and damaging the blood corpuscles, thus avoiding haemolysis or, it will not mix with other solutions which are added to the blood and for this reason cross reactions will be prevented. Since polypropylene glycol also has surface-tension reducing properties the intermixture of blood with other fluids is improved and the use of mechanical mixing appliances may be avoided. The same results are achieved in continuous-flow systems, when the tube is treated with polypropylene glycol or if polypropylene glycol is added to the fluids propelled inside a tube of this kind. Thus, less energy-consuming pumps may be used.

Figure 4:
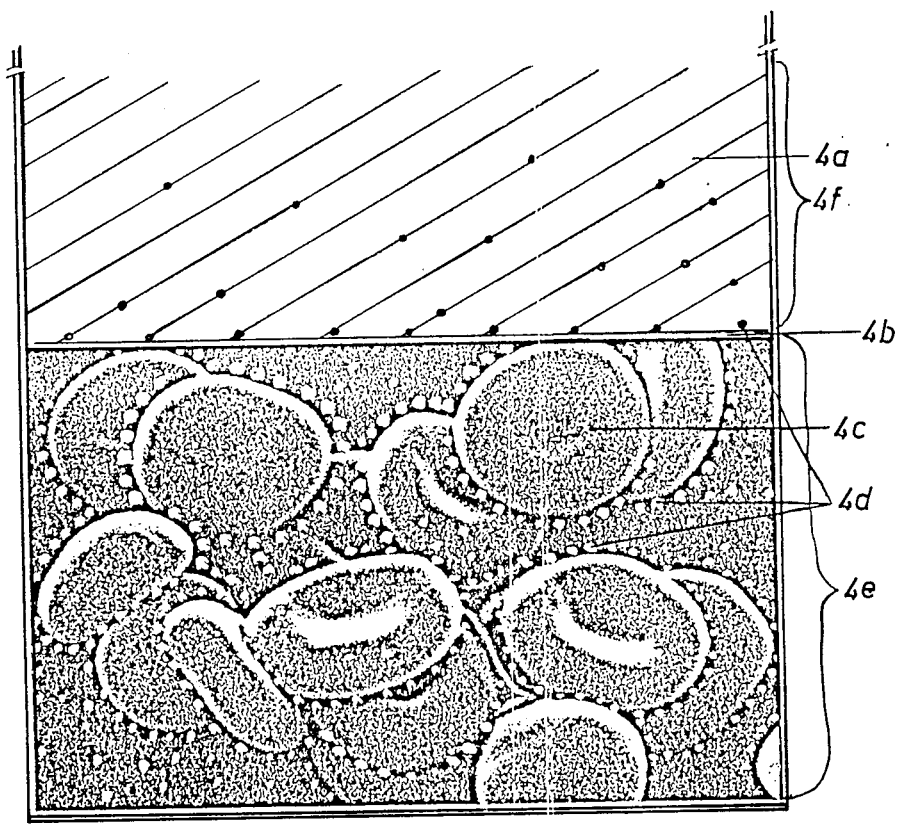
FIG. 4 shows the sedimentation reaction of erythrocytes forming stacked-coin clusters and surrounded by polypropylene glycol (4d) which neutralizes the repellent forces existing between the erythrocytes and between the blood corpuscle column (4e) and the plasma column (4f), creating a flat interface (4b) between the sedimented erythrocytes and the plasma (4a) on top thereof.

Polypropylene glycol mixed with blood to which citrate has been added to effect the erythrocyte sedimentation rate test (ESR) enhances the formation of the erythrocytes in "rouleaux formation" clusters and this is due to the polypropylene glycol neutralizing the repellent forces existing between the erythrocytes which aggregate in stacked-coin clusters and which are negatively charged by nature. Consequently, the formation into stacked coin clusters is facilitated. Considering that polypropylene glycol also is instrumental in reducing surface tension the interface between sedimented erythrocytes in the ESR column and the plasma becomes flat rather than concave and consequently reading faults are avoided (FIG. 4).

The invention belongs to the medical technical and analytical fields wherein capillary tubes are used for mixture or transport of blood and/or other fluids.

Capillary tubes are used both for blood collection and for addition to the very same tube of a further fluid. The fluids are mixed with each other with the aid of a gas bubble and repeated turning-over of the capillary tube. However, because the inertia of intermixing is considerable, mechanical means must often be used to assist in the intermixing, which easily can cause damage to the erythrocytes of the blood.

Also transport and propulsion of blood or other fluid in the lengthwise direction inside the capillary tube, such as is the case in e.g. continuous-flow systems, is both difficult and energy-consuming because of the strong surface tension present in such tubes. It therefore becomes necessary to use liquid-propulsion mechanisms which easily could damage the erythrocytes. For this reason larger-bore capillary tubes are often used to reduce the surface tension.

The purpose of the subject invention is to reduce the surface tension inside capillary tubes, thereby increasing the ability of blood and other fluids to intermix or increasing their movability therein without altering the character of either the blood or the other fluids.

This problem is solved in that to the capillary tube or to the fluids contained in the tube is added polypropylene glycol which reduces the surface tension and the electro-static forces. Fluids therefore flow more easily through the tube and use much less energy while at the same time the intermixing is effected more rapidly and more efficiently.

In analytical methods according to which fluids contained in a capillary tube are sedimented so that an interface is formed between the sediment and the layer on top, this interface will become flat on account of the surface-tension reducing and the electrostatically repellant effects of polypropylene glycol. In addition, the polypropylene glycol will act as a foam-reducing agent.

The invention is primarily intended for use within the medical technology and analytical field or in any other technology wherein capillary tubes are used for mixing fluids inside such tubes or to transport fluids through such tubes without alteration of the character of the fluids, such as is the case in e.g. dispensing devices, through-flow analytical devices, flow cuvettes, infusion or transfusion units or in capillary analysis tubes for laboratory uses.

The expert in the field readily understands that the applications referred to above may be varied in many ways within the scope of the appended claims.

What we claim is:

1. An improved method of handling blood and blood solutions in a capillary tube by reducing the electrostatic forces acting on the blood and blood solutions by adding propylene glycol to the blood and blood solutions to reduce its surface tension without cross-reacting with the blood and blood solutions.

2. An improved method claimed in claim 1, wherein said handling comprises conducting said blood and blood solutions through said capillary tube.

3. An improved method as claimed in claim 1, wherein said handling comprises the intermixing of said blood and blood solutions with a second fluid.

4. An improved method as claimed in claim 3, wherein said intermixing comprises mixing blood with a second fluid designed to facilitate dispersion of the blood in said second fluid.

5. An improved method of performing analyses involving sedimentation of particles of blood in a liquid in a capillary tube by adding propylene glycol to said liquid containing blood particles to reduce the repellent forces existing between said particles forming said sediment without cross-reacting with said particles of blood.

6. An improved method as claimed in claim 5, comprising adding polypropylene glycol to said particles in said liquid, wherein said particle are red blood cells and said sedimentation includes the formation of rouleaux of clustered red blood cells.

* * * * *